United States Patent [19]
Bryant et al.

[11] Patent Number: 5,119,029
[45] Date of Patent: Jun. 2, 1992

[54] EASILY CLEANED STREAMING CURRENT MONITOR

[76] Inventors: Robert L. Bryant, 5166 Meadow Creek Dr., Dunnwoody, Ga. 30338; Charles R. Veal, 5501 Shawnee Trail, Norcross, Ga. 30071

[21] Appl. No.: 664,305

[22] Filed: Mar. 4, 1991

[51] Int. Cl.⁵ .......................................... G01N 27/60
[52] U.S. Cl. ................................... 324/453; 324/71.1
[58] Field of Search ...................... 324/71.1, 453, 452, 324/446–450

[56] References Cited

U.S. PATENT DOCUMENTS 4,446,435  5/1984  Canzoneri ...................... 324/71.1 X
4,769,608  9/1988  Bryant ................................ 324/453

*Primary Examiner*—Jack B. Harvey
*Attorney, Agent, or Firm*—Harry I. Leon

[57] ABSTRACT

A streaming current detector having a probe with an electrode holder which can be removed and replaced within only about one minute, allowing the probe to be kept on line nearly continuously even in highly contaminated wastewater. The probe also includes a reciprocating piston and a housing with both a cylindrical void and a transverse passageway. In assembled relation, the electrode holder is slidably disposed within the cylindrical void; and the piston is slidably engaged with an inner wall of the electrode holder. Capillary-sized channels formed between this inner wall and the piston communicate fluidly with the transverse passageway. From it, any test flow stream present is partially sucked into the capillary-sized channels during an upstroke of the piston and then expelled from them, back into the transverse passageway, during the succeeding downstroke. Lacking any low velocity or stagnate areas in the transverse passageway or in the capillary-sized channels, solids cannot accumulate in the probe, making it almost self-cleaning. But, in severely contaminated waters, the electrodes in the probe still tend to foul. With the detector, electrode replacement is readily accomplished: a retaining fitting is removed, the electrode holder is slid out of the flow member, a clean electrode holder is slid into position, and the retaining fitting is replaced.

7 Claims, 4 Drawing Sheets

EASILY CLEANED STREAMING CURRENT MONITOR

BACKGROUND OF THE INVENTION

The present invention relates to an improved streaming current detector and in particular to an apparatus for measuring the average net ionic colloidal surface charge on the surface of an annulus formed of a dielectric material, the charge being a function of the charge influencing species, such as ions, charged molecules or colloidal particles, which are present in a liquid stream in flowing contact with said dielectric surface.

It is well known most waters contain ions and other charged particles species such as colloids and that when certain chemicals are employed to treat the water, contaminates in the water will form aggregates and settle out of the water as a floc. But any floc which forms has a tendency to stick to every surface with which it comes into contact.

A useful quantity for controlling the amount of chemicals needed to treat water is the streaming current, a current generated when a dielectric surface, in the presence of charged species in water, is moved past a pair of electrodes. Unfortunately, if any contaminants are allowed to build up on either the electrodes or a surface disposed proximate to the electrodes, the streaming current cannot be reliably measured.

Many attempts have been made at keeping the electrodes of a streaming current detector clean during operation. One of the latest is disclosed by Bryant and Veal in U.S. Pat. No. 4,769,608. There Bryant and Veal disclosed a self-cleaning probe for a streaming current detector in which the electrodes are mounted within a flowpath member. A test flow stream enters this probe along a transverse passageway. A small portion of the flow is then alternately sucked, by the action of a piston, into capillary-sized channels formed between an inner wall of the flowpath member and the piston and expelled back into the transverse passageway. Leaving the passageway, the flow stream plummets downwardly through housing surrounding the probe before being finally discharged.

The probe and probe housing in the Bryant and Veal device disclosed in U.S. Pat. No. 4,769,608 are designed so that there are no low flow velocity or stagnate areas where solids can accumulate. Floc which does come in contact with the probe is constantly washed off by the rapidly moving flow stream. In spite of this constant washing action, however, the applicants have found that the probe must be cleaned periodically, especially when the probe is used to measure the streaming current of highly contaminated wastewater.

This periodic cleaning is required because the electrodes themselves within the probe tend to foul over time. In the cited prior art combination, cleaning the probe required the operator to turn off the streaming current detector, disassemble it, clean or replace the entire flowpath member, and then reassemble the detector. Much time was wasted, necessitating a costly shutdown of the process which the detector was regulating.

SUMMARY OF THE INVENTION

An object of the present invention is to provide a streaming current detector which not only has a flow pattern in the vicinity of the probe that keeps the electrodes therein and the dielectric surfaces proximate to these electrodes free from floc buildup that would otherwise interfere with the electrical output from the electrodes but also has a holder for the electrodes which can be removed and replaced in less than one minute, so that the probe can be kept on line nearly continuously.

In accordance with the present invention, there is provided a very stable and reliable detector for the measurement of the streaming current in water or wastewater that can be operated over long periods of time without having to be shut down for cleaning. The detector includes a probe with a holder in which the electrodes are mounted and a housing. In use, the housing forms a sheath for the holder which is slidably insertable within a cylindrical void formed in the housing. When cleaning becomes necessary, the electrodes, as well as the dielectric surface contiguous with them in the holder, can be removed and replaced in less than one minute.

The holder is secured within the housing by a single retaining fitting which, in use, is threadedly engaged with external threads on the lower end of the housing. A shoulder on the holder forms a stop which abuts the lower end of the housing when the holder is inserted as far as possible into the housing. In the assembled detector, as the retaining fitting is tightened on the threads which engage it with the housing, the retaining fitting causes the shoulder to press against the lower end of the housing, forming a leak-tight seal with it.

The housing defines a transverse passageway through which a test flow stream is directed. Samples of the test flow stream are alternately sucked into capillary-sized channels within a piston-electrode chamber directly beneath the passageway and expelled from these channels. The test flow stream flowing in the transverse passageway moves over the entrances to these channels with sufficient velocity to wash away any floc that might form on the top of these entrances.

In addition, the test flow stream after leaving the transverse passageway drops immediately into a drain channel directed downwardly and away from the probe so that neither floc nor grit can build up in the vicinity of the probe. Any floc or grit present either remains suspended in the test flow stream or is promptly washed away. In this way, the measuring electrodes and the surfaces of the probe around them are kept free from all but a slow fouling which takes place over an extended period of time. Not only is the frequency of any shutdown for cleaning with this improved detector very low but the actual downtime for any such cleaning is minimal.

DETAILED DESCRIPTION OF THE PREFERRED EMBODIMENT

Figure 1:
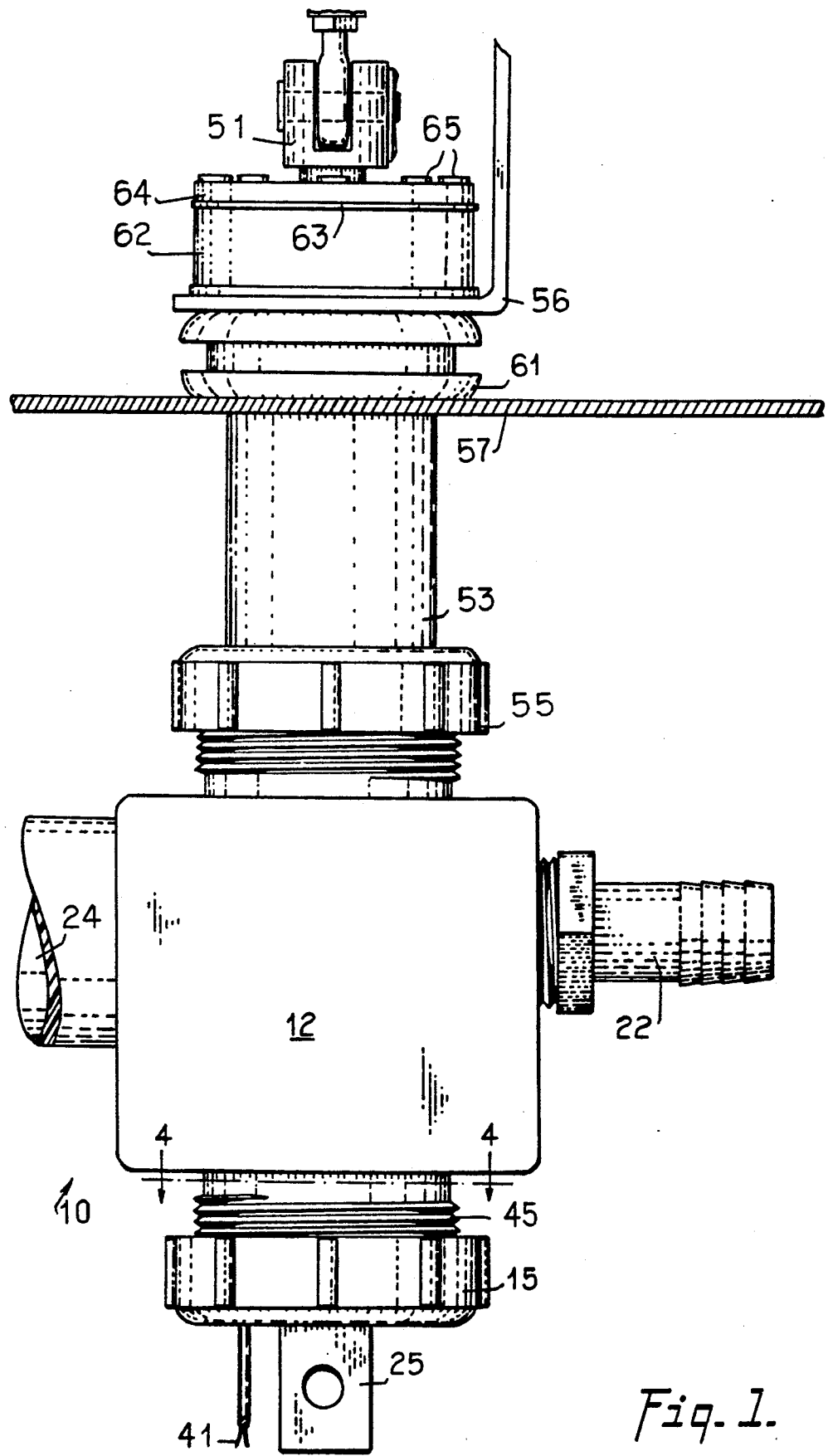
FIG. 1 is a frontal elevation view of a fragmentary portion of the streaming current detector, including the probe, according to the present invention.

As illustrated in FIGS. 1 through 3 and 5, an apparatus, which is indicated generally by the numeral 10, comprises a probe 11 that includes a housing 12 with a cylindrical void 13 for slidably receiving a holder 14. The holder 14 itself has an inner wall 19 which defines a bore 16. In assembled relation, the holder 14 is mounted within the void 13 and secured in place there by a retaining fitting 15. In the preferred embodiment, the fitting 15 threadedly engages external threads 45 on the lower end of the housing 12. Upon removal of the fitting 15, the holder 14 can be quickly slid out of the housing 12 and replaced with another holder.

Notwithstanding the ease of disengagement of the holder 14 from the housing 12, there is a close fit between the sides of the cylindrical void 13 and the holder. The inner and outer diameters of the void 13 and the holder 14 measure, by way of example, 1.500 and 1.510 inches, respectively. Fluid, which might otherwise seep between the holder 14 and the housing 12 and leak from the probe 11, is restrained from such activity by a shoulder 37 formed at the base of the holder. The shoulder 37 abuts the lower end of the housing 12 when the fitting 15 is tightened so that its engages, to the maximum extent, the external threads 45 on the lower end of the housing.

Figure 2:
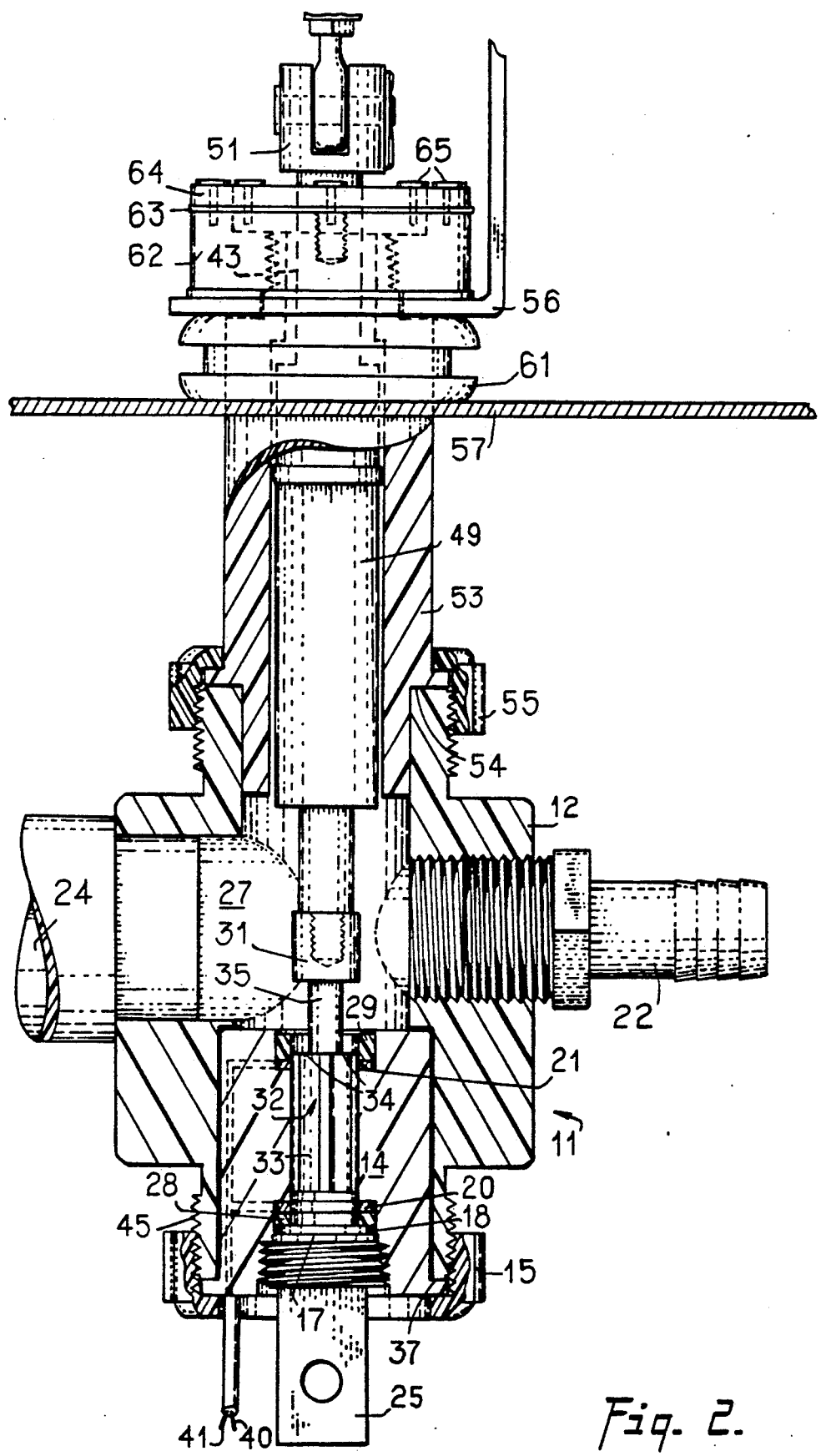
FIG. 2 is longitudinal cross-section through the detector according to FIG. 1 in which the piston is at the top of its stroke.
Figure 3:
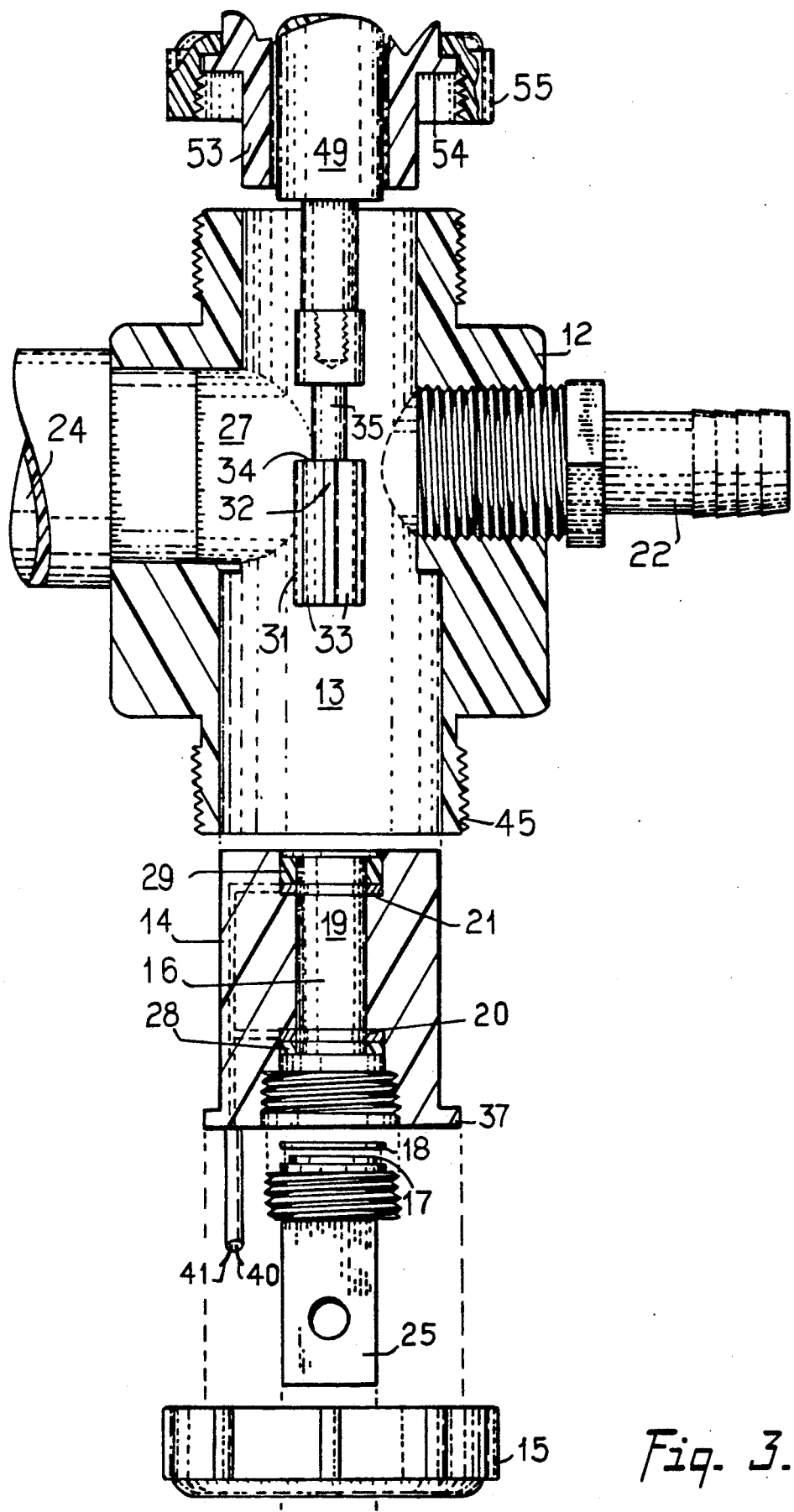
FIG. 3 is an exploded view of a segment of the longitudinal cross-section according to FIG. 2.

The apparatus 10 further comprises a piston 31 with an active segment 32 which fits snugly in the bore 16. In the preferred embodiment, the maximum span of each of the transverse cross-sections of the active segment 32 as well as of the bore 16 measures approximately 0.505 inches. The piston 31 and the holder 14 are preferably made from delrin due to its dielectric properties, low surface friction coefficient, low surface adsorption and ease in machining. Longitudinal grooves 33 formed in the active segment 32 extend the length thereof, allowing flow between it and the active segment. The bottom of the bore 16 is a cylinder head 17 which, in the preferred embodiment, threadedly engages the holder 14 below the maximum travel of the piston 31. As is best seen in FIG. 2, an 0-ring 18 that surrounds the upper edges of the head 17 fills a groove proximate with the lower end of the bore 16 when the head is seated in the holder 14, so that the 0-ring forms a leaktight seal between the holder and the head.

Ring electrodes 20, 21 fit into grooves formed in the bore 16 and are spaced from each other a distance approximately equal to the length of the active segment 32 of the piston 31. The electrodes 20, 21 and lead wires 40, 41 connected to them are the only metallic elements in the probe 11. The electrodes 20, 21 are preferably made of stainless steel and secured within the holder 14 by annuli 28, 29, respectively, formed of a dielectric material, such as that from which the bulk of the holder 14 is fabricated. The annulus 29 is preferably affixed to the holder with the use of adhesive. Channels within the holder 14 for the lead wires 40, 41 are sealed with glue or a potting compound (not shown). As the piston 31 moves, charged colloids and ions in any fluid present within the grooves 33 induce opposite and equal charges on the dielectric surfaces of the piston 31 and of the holder 14 which flow in part to the electrodes 20, 21 and which give rise to an electrical signal known as the streaming current.

As is illustrated in FIGS. 1 through 3 and 5, probe 11 also includes an inlet nozzle 22 and a transverse passageway 27. The housing 12 defines the transverse passageway 27 which fluidly interconnects the nozzle 22 and a drain channel 24. The nozzle 22 is provided for feeding a test flow stream into the probe 11. As it moves through the transverse passageway 27, the stream washes the top of the active segment 32 of the piston 31. A waist 35 formed in the piston 31 above the grooves 33 gives rise to a higher flow velocity in the vicinity of the top of the active segment 32 than would otherwise occur, thereby facilitating washing suspended material such as floc away from this top.

When the piston 31 moves up, a small portion of the flow entering the transverse passageway 27 is pulled into capillary-sized channels 23 formed between the inner wall 19 of the holder 14 and wall sections of the grooves 33 in the piston 31. The forces acting on the flow as it enters these channels are due not only to a vacuum created in the vicinity of the cylinder head 17 on the upstroke of the piston 31 but also to a positive pressure created at the upper ends 34 of the capillary grooves 33 by the placement of these ends in direct contact with the flow stream in the passageway 27. During the downstroke of the piston 31, fluid within the grooves 33 is expelled back into the passageway 27.

Means for forcing the piston 31 into repetitive upward and downward motions comprises a guide 49. As is illustrated in FIG. 2, the piston 31 is threadedly engaged with the guide 49. The guide 49 in turn is threadedly engaged with a yoke 51 which is pinned to a crank 42. The threaded connections between the guide 49 and the piston 31 and between the guide 49 and the yoke 51 facilitate alternately disassembling and reassembling of the probe 11.

From the yoke 51, the guide 49 extends downwardly through a screw cap 62, grommet 61 and barrel member 53 to the transverse passageway 23. The barrel member 53 is, in large part, mounted atop the housing 12; but a lower portion of the barrel member is mounted within the housing and is slidably removable therefrom. The extension of the barrel member 53 into the housing 12 is limited by a stop 54, contiguous with this lower portion, which protrudes from the outer wall of the barrel member 53 (FIG. 2). The stop 54 is preferably concentric with the remainder of the barrel member 53. A connector 55, which encircles the barrel member 53 above the stop 54, is employed to threadedly engage the upper end of the housing 12 and, simultaneously, to press the stop 54 against the housing, creating a leaktight joint between the barrel member and the housing.

Upwardly of the connector 55, the barrel member 53 is disposed within the grommet 61 which is sandwiched between a protective casing 57 and a bracket 56. Circular openings of approximately the same diameter are provided both in the casing 57 and in the grommet 61. In the assembled detector, the centers of these two openings are aligned longitudinally with the center of a third circular opening of substantially smaller diameter formed in the bracket 56. Threads for engaging the screw cap 62 are provided on the upper end of the barrel member 53, which extends through this third opening. As the screw cap is tightened, the portion of the barrel member 53 situated downwardly of the bracket 56 is pressed against it.

The juncture between the yoke 51 and the guide 49 is situated slightly below a plate 64 affixed to the screw cap 62. This plate 64 is employed to secure a diaphram 63 in place. The diaphragm 63, which is fabricated from rubber or the like, defines an aperture of approximately the same diameter as the lower end of the yoke 51. In the apparatus 10, the lower end of the yoke 51 extends through this aperture in the diaphragm 63. The diaphragm 63 prevents the migration of any fluid from the transverse passageway 27 through the barrel member 53 and the screw cap 62 to the interior of the protective casing 57.

Figure 5:
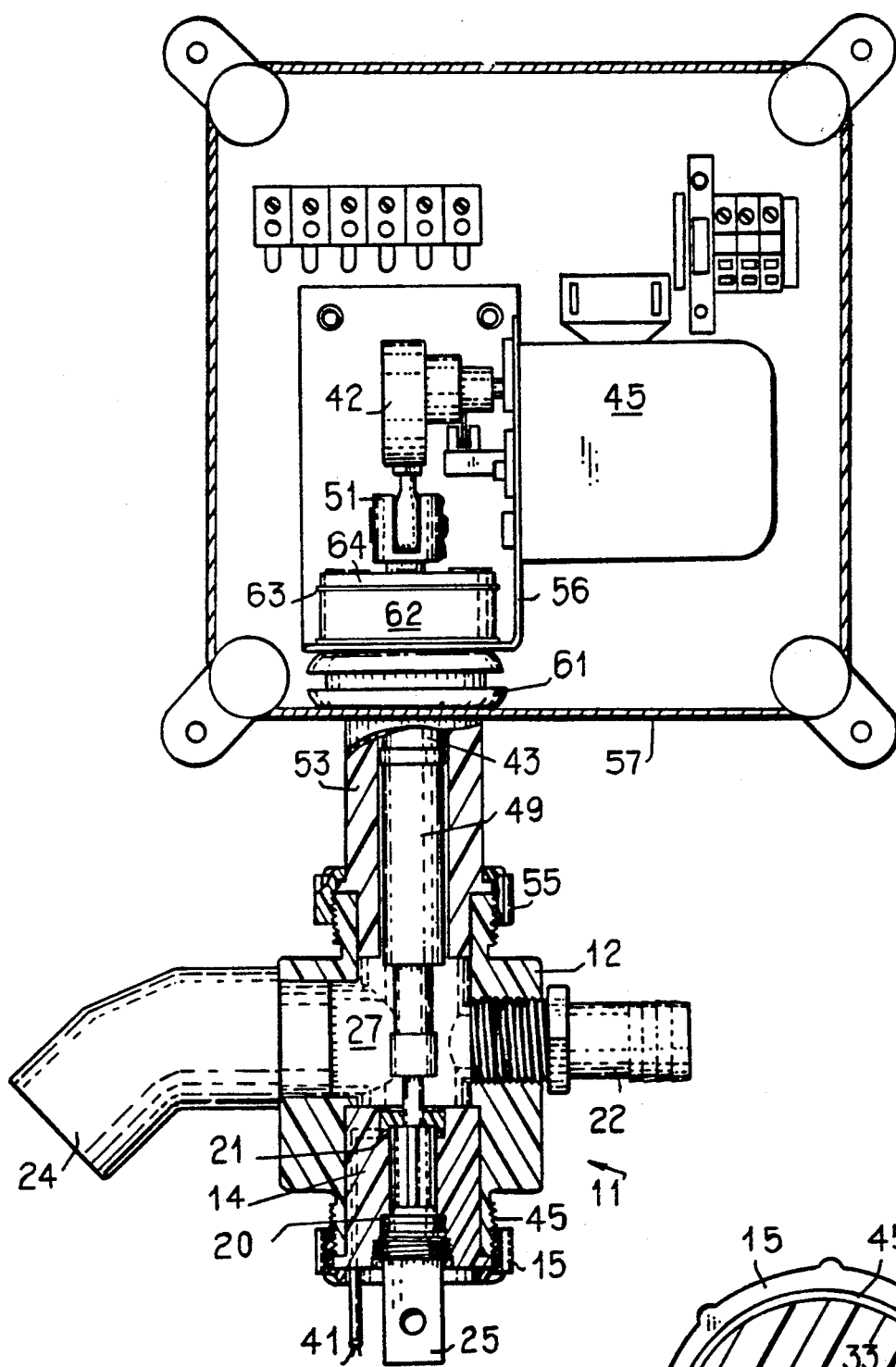
FIG. 5 is a frontal elevation view, partially in longitudinal cross-section and on a reduced scale, of the streaming current detector according to the present invention.
Figure 4:
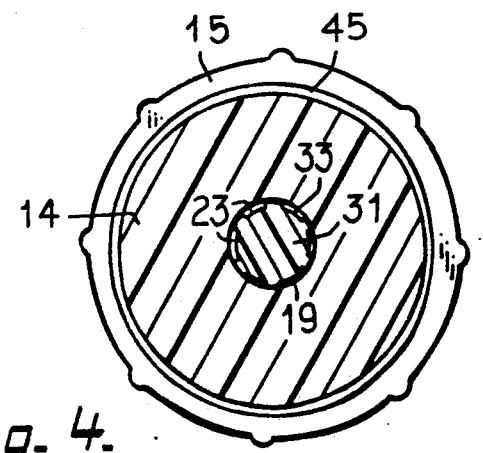
FIG. 4 is a cross-section 4—4 through the probe in FIG. 1.

Acting through the yoke 51 and the guide 49 to force the piston 31 into repetitive upward and downward motions, the crank 42 is driven by a synchronous motor 45 at a constant rpm (FIG. 5). This rotational speed is preferably 240 rpm. Means for generating a square wave signal as the crank is rotated is described in U.S. Pat. No. 4,769,608. A square wave signal is used to facilitate the detection of an alternating current generated when first one end of the active segment 32 of the piston 31 passes one of the electrodes 20, 21 and then the other end of this active segment passes one of these electrodes.

As an end of the active segment 32 of the piston 31 moves into the vicinity of the one of the electrodes 20, 21, an additional charge is induced on the electrodes. An alternating current is generated at the frequency of the reciprocating motion of the piston 31. The alternating current generated is proportional to the net charge density on the colloids and ions in the test flow stream and is known as the streaming current. Means, including a filtering and synchronized measurement circuit, for processing this alternating signal to provide input to an indicating and control circuit (not shown) is disclosed in U.S. Pat. No. 4,769,608. With the present invention, the strength of the streaming current signal generated is sufficient to have a readout and control device remotely situated at distances of up to 1000 feet from the apparatus 10.

Having described the invention, what is claimed is:

1. In an apparatus for determining a function of the electric charge condition in a flowable liquid media containing electrical charge influencing species, said apparatus comprising:
   a. a housing having a transverse passageway with an inlet and an exit disposed at opposite ends thereof, the passageway being disposed so that it may be substantially filled with said flowable liquid media, the housing including a cylindrical void disposed perpendicularly to the transverse passageway and to one side thereof;
   b. a holder made of an electrically insulating material, the housing forming a sheath for the holder when the holder is inserted into the cylindrical void, the holder being slidably removable from the cylindrical void;
   c. means for retaining the holder in a fixed position relative to the housing, the holder being removable from the housing without disturbing any connections for the inlet to and the exit from the transverse passageway, so that the holder can be easily and quickly removed for cleaning;
   d. a reciprocating element whose outer wall, at least, is electrically insulating and which is disposed in slidable relationship with said holder, said reciprocating element having an active segment, the active segment having a transverse cross-section such that the segment fits adjacent to but has a plurality of wall sections spaced from the contiguous wall of the holder, so that the active segment and the holder form capillary-sized flow channels when the element reciprocates in said holder;
   e. a pair of sensing eletrodes located within the holder which are spaced apart from each other, the first said sensing electrode being located near the transverse passageway with both electrodes being so disposed as to be contacted by said flowable liquid media entering or leaving said flow channels;
   f. means for moving the reciprocating element in said holder so that the element reciprocates at a constant frequency; and
   g. means coupled to said electrodes for detecting an alternating current flowing between said electrodes that is generated at the frequency of the reciprocating element.

2. The apparatus according to claim 1 wherein the retaining means comprises a retaining fitting threadedly engageable with the housing.

3. The apparatus according to claim 2 wherein the holder further comprises a shoulder which abuts the lower end of the housing when the holder is inserted as far as possible into the cylindrical void, the shoulder being seated within the retaining fitting and being pressed against the lower end of the housing when the retaining fitting is threadedly engaged to a sufficient degree with the housing.

4. The apparatus according to claim 1 which further comprises means for admitting said flowable liquid media into said housing so that there is no stagnation within the flow of the liquid media proximate entrances to said flow channels.

5. The apparatus according to claim 1 which further comprises means for directing the discharge of the flowable liquid media from said passageway away from the housing.

6. The apparatus according to claim 1 wherein the active segment of the reciprocating element is further characterized as having grooves which extend longitudinally along the length of the active segment, the grooves and the wall of the holder forming said capillary-sized channels.

7. An apparatus for measuring the streaming current in a sample flow stream of a fluid containing charged species such as ions and colloids comprising:
   a. a housing having a transverse passageway, an inlet thereto, and an exit therefrom through which the stream can flow;
   b. a holder made of an electrically insulating material, the holder being substantially disposed within the housing and slidably removable therefrom;
   c. means for retaining a substantial portion of the holder within the housing, the holder being removable from the housing without disturbing any connections for the inlet to and the exit from the transverse passageway, so that the holder can be easily and quickly removed for cleaning;
   d. a reciprocating element whose outer wall, at least, is electrically insulating and which is disposed in slidable relationship with said holder, said reciprocating element having an active segment, the active segment having a transverse cross-section such that the segment fits adjacent to but has a plurality of wall sections spaced from the contiguous wall of the holder, so that the holder and the active segment form capillary-sized flow channels when the element reciprocates in said holder, the capillary-sized flow channels being fluidly connected to the transverse passageway, entrances to the channels being washed by the stream flowing through the passageway;

e. a pair of sensing electrodes located within the holder which are spaced apart from each other, the first said sensing electrode being located near the transverse passageway, both electrodes being so disposed as to be contacted by the fluid entering or leaving said flow channels;

f. means for moving the reciprocating element in said holder so that the element reciprocates at a constant frequency; and g. means coupled to said electrodes for detecting an alternating current flowing between said electrodes that is generated at the frequency of the reciprocating element.

* * * * *